United States Patent [19]

Ingram et al.

[11] Patent Number: 5,000,000

[45] Date of Patent: Mar. 19, 1991

[54] **ETHANOL PRODUCTION BY *ESCHERICHIA COLI* STRAINS CO-EXPRESSING *ZYMOMONAS* PDC AND ADH GENES**

[75] Inventors: Lonnie O. Ingram, Gainesville, Fla.; Tyrrell Conway, Lincoln, Nebr.; Flavio Alterthum, Gainesville, Fla.

[73] Assignee: University of Florida, Gainesville, Fla.

[21] Appl. No.: 352,062

[22] Filed: May 15, 1989

Related U.S. Application Data

[63] Continuation-in-part of Ser. No. 239,099, Aug. 31, 1988, abandoned.

[51] Int. Cl.$^5$ .................. C12P 7/06; C07H 15/12; C12N 15/00
[52] U.S. Cl. .................. 435/161; 435/172.3; 435/320.1; 435/252.3; 435/252.33; 435/170; 536/27; 935/19; 935/29; 935/40; 935/60
[58] Field of Search .................. 435/161, 170, 172.3, 435/320, 253, 252.33, 252.3; 536/27; 935/27, 19, 40, 60, 41, 29, 73

[56] References Cited

PUBLICATIONS

Fried, V. A., A. Novick (1973) "Organic Solvents as Probes for the Structure and Function of the Bacterial Membrane: Effects of Ethanol on the Wild Type and an Ethanol-Resistant Mutant of *Escherichia coli* K-12," J. Bacteriol. 114(1):239-248.

Ingram, L. O. (1976) "Adaptation of Membrane Lipids to Alcohols," J. Bacteriol. 125(2):670-678.

Ingram, L. O., N. S. Vreeland (1980) "Differential Effects of Ethanol and Hexanol on the *Escherichia coli* Cell Envelope," J. Bacteriol. 144(2):481-488.

Ingram, L. O., T. M. Buttke (1984) "Effects of Alcohols on Micro-Organisms," in *Advances in Microbial Pathology*, vol. 25, Academic Press, London, pp. 254-295.

Bringer-Meyer, S., K.-L. Schimz, and H. Sahm (1986) "Pyruvate Decarboxylase from *Zymomonas mobilis*. Isolation and Partial Characterization," Arch. Microbiol. 146:105-110.

Brau, B. and H. Sahm (1986) "Cloning and Expression of the Structural Gene for Pyruvate Decarboxylase of *Zymomonas mobilis* in *Escherichia coli*," Arch. Microbiol. 144:296-301.

Conway, T., Y. A. Osman, J. I. Konnan, E. M. Hoffmann, and L. O. Ingram (1987) "Promoter and Nucleotide Sequences of the *Zymomonas mobilis* Pyruvate Decarboxylase," J. Bacteriol. 169:949-954.

Conway, T., G. W. Sewell, Y. A. Osman and L. O. Ingram (1987) "Cloning and Sequencing of the Alcohol Dehydrogenase II Gene from *Zymomonas mobilis*," J. Bacteriol. 169:2591-2597.

Neale, A. D., R. K. Scopes, R. E. H. Wettenhall and N. J. Hoogenraad (1987) "Nucleotide Sequence of the Pyruvate Decarboxylase Gene from *Zymomonas mobilis*," Nucleic Acids Res. 15:1753-1761.

Ingram, L. O. and T. Conway (1988) "Expression of Different Levels of Ethanologenic Enzymes from *Zymomonas mobilis* in Recombinant Strains of *Escherichia coli*," Appl. Environ. Microbiol. 54:397-404.

Ingram, L. O., T. Conway, D. P. Clark, G. W. Sewell, and J. F. Preston (1987) "Genetic Engineering of Ethanol Production in *Escherichia coli*," Appl. Environ. Microbiol. 53:2420-2425.

Tolan, J. S. and R. K. Finn (1987) "Fermentation of D-Xylose and L-Arabinos to Ethanol by *Erwinia chrysanthemi*," Appl. Environ. Microbiol. 53:2033-2038.

Tolan, J. S. and R. K. Finn (1987) "Fermentation of D-Xylose to Ethanol by Genetically Modified *Klebsiella planticola*," Appl. Environ. Microbiol. 53:2039-2044.

*Primary Examiner*—Robin L. Teskin
*Attorney, Agent, or Firm*—Saliwanchik & Saliwanchik

[57] ABSTRACT

A novel operon and plasmids comprising genes which code for the alcohol dehydrogenase and pyruvate decarboxylase activities of *Zymomonas mobilis* are described. Also disclosed are methods for increasing the growth of microorganisms or eukaryotic cells and methods for reducing the accumulation of undesirable metabolic products in the growth medium of microorganisms or cells.

7 Claims, 4 Drawing Sheets

SYMBOLS: ■, pLOI295; ●, pLOI308-2; ○, pLOI308-5;
▲, pLOI308-10; □, STRAIN TC4 LACKING A PLASMID

FIG. 4

SYMBOLS: ▲, AEROBIC GROWTH CONDITIONS;
●, ANAEROBIC GROWTH CONDITIONS

ETHANOL PRODUCTION BY *ESCHERICHIA COLI* STRAINS CO-EXPRESSING *ZYMOMONAS* PDC AND ADH GENES

This invention was made with government support under the following grants: USDA Alcohol Fuels Program #86CRCR12134 and DOE Office of Basic Energy FG05-86ER3574. The government has certain rights in this invention.

CROSS-REFERENCE TO A RELATED APPLICATION

This application is a continuation-in-part of our copending application Ser. No. 239,099, filed Aug. 31, 1988, now abandoned.

DESCRIPTION

Background of the Invention

During glycolysis, cells convert simple sugars, such as glucose, into pyruvic acid, with a net production of ATP and NADH. In the absence of a functioning electron transport system for oxidative phosphorylation, at least 95% of the pyruvic acid is consumed in short pathways which regenerate NAD+, an obligate requirement for continued glycolysis and ATP production. The waste products of these NAD+ regeneration systems are commonly referred to as fermentation products.

Microorganisms are particularly diverse in the array of fermentation products which are produced by different genera (Krieg, N. R., and J. G. Holt, eds. [1984] *Bergey's Manual of Systematic Bacteriology*. The Williams & Wilkins Co., Baltimore). These products include organic acids, such as lactate, acetate, succinate, and butyrate, as well as neutral products, such as ethanol, butanol, acetone, and butanediol. Indeed, the diversity of fermentation products from bacteria has led to their use as a primary determinant in taxonomy (Krieg and Holt [1984], supra).

End products of fermentation share several fundamental features. They are relatively nontoxic under the conditions in which they are initially produced but become more toxic upon accumulation. They are more reduced than pyruvate because their immediate precursors have served as terminal electron acceptors during glycolysis. The microbial production of these fermentation products forms the basis for our oldest and most economically successful applications of biotechnology and includes dairy products, meats, beverages, and fuels. In recent years, many advances have been made in the field of biotechnology as a result of new technologies which enable researchers to selectively alter the genetic makeup of some microorganisms.

*Escherichia coli* is an important vehicle for the cloning and modification of genes for biotechnology and is one of the most important hosts for the production of recombinant products. In recent years, the range of hosts used for recombinant DNA research has been extended to include a variety of bacteria, yeasts, fungi, and some eukaryotic cells. The invention described here relates to the use of recombinant DNA technology to elicit the production of specific useful products by a modified host.

The DNA used to modify the host of the subject invention is isolated from *Zymomonas mobilis*. *Z. mobilis* is a microorganism with unusual metabolic characteristics which is commonly found in plant saps and in honey. *Z. mobilis* has long served as a natural inocula for the fermentation of the Agave sap to produce pulque (an alcohol-containing Mexican beverage) and as inocula for palm wines. This organism is also used for fuel ethanol production and has been reported capable of ethanol production rates which are substantially higher than that of yeasts.

Although *Z. mobilis* is nutritionally simple and capable of synthesizing amino acids, nucleotides and vitamins, the range of sugars metabolized by this organism is very limited and normally consists of glucose, fructose and sucrose. Substrate level phosphorylation from the fermentation of these sugars is the sole source of energy for biosynthesis and homeostasis. *Z. mobilis* is incapable of growth even in rich medium such as nutrient broth without a fermentable sugar.

*Z. mobilis* is an obligately fermentative bacterium which lacks a functional system for oxidative phosphorylation. This organism, like *Saccharomyces cerevisiae*, produces ethanol and carbon dioxide as principal fermentation products. *Z. mobilis* produces ethanol by a short pathway which requires only two enzymatic activities: pyruvate decarboxylase and alcohol dehydrogenase. Pyruvate decarboxylase is the key enzyme in this pathway which diverts the flow of pyruvate to ethanol. Pyruvate decarboxylase catalyzes the nonoxidative decarboxylation of pyruvate to produce acetaldehyde and carbon dioxide. Two alcohol dehydrogenase isozymes are present in this organism and catalyze the reduction of acetaldehyde to ethanol during fermentation, accompanied by the oxidation of NADH to NAD+. Although bacterial alcohol dehydrogenases are common in many organisms, few bacteria have pyruvate decarboxylase. Attempts to modify *Z. mobilis* to enhance its commercial utility as an ethanol producer have met with very limited success.

Most fuel ethanol is currently produced from hexose sugars in corn starch or cane syrup utilizing either *Saccharomyces cerevisiae* or *Zymomonas mobilis*. However, these are relatively expensive sources of biomass sugars and have competing value as foods. Starches and sugars represent only a fraction of the total carbohydrates in plants. The dominant forms of plant carbohydrate in stems, leaves, hulls, husks, cobs, etc. are the structural wall polymers, cellulose and hemicellulose. Hydrolysis of these polymers releases a mixture of neutral sugars which include glucose, xylose, mannose, galactose, and arabinose. No single organism has been found in nature which can rapidly and efficiently metabolize these sugars into ethanol or any other single product of value.

The genes coding for alcohol dehydrogenase II and pyruvate decarboxylase in *Z. mobilis* have been separately cloned, characterized, and expressed in *E. coli* (Bräu, B., and H. Sahm [1986] Arch. Microbiol. 146:105-110; Bräu, B. and H. Sahm [1986] Arch. Microbiol. 144:296-301; Conway, T., Y. A. Osman, J. I. Konnan, E. M. Hoffmann, and L. O. Ingram [1987] J. Bacteriol. 169:949-954; Conway, T., G. W. Sewell, Y. A. Osman, and L. O. Ingram [1987] J. Bacteriol. 169:2591-2597; Neale, A. D., R. K. Scopes, R. E. H. Wettenhall, and N. J. Hoogenraad [1987] Nucleic Acid. Res. 15:1753-1761; Ingram, L. O., and T. Conway [1988] Appl. Environ. Microbiol. 54:397-404; Ingram, L. O., T. Conway, D. P. Clark, G. W. Sewell, and J. F. Preston [1987] Appl. Environ. Microbiol. 53:2420-2425).

Bräu and Sahm (Bräu, B. and H. Sahm [1986] Arch. Microbiol. 144:296-301) first demonstrated that ethanol production could be increased in recombinant *E. coli* by the over-expression of *Z. mobilis* pyruvate decarboxylase although very low ethanol concentrations were produced. Subsequent studies by Tolan and Finn extended this work by using two other enteric bacteria (*Erwinia chrysanthemi,* Tolan, J. S. and R. K. Finn [1987] Appl. Environ. Microbiol. 53:2033-2038; *Klebsiella planticola,* Tolan, J. S. and R. K. Finn [1987] Appl. Environ. Microbiol. 53:2039-2044) and achieved higher levels of ethanol from hexoses, pentoses, and sugar mixtures. The subject invention relates to the creation and expression of a novel operon coding for an efficient ethanol-producing system. This novel operon can be used to transform microorganisms in order to confer upon the transformed microbes the capability of producing ethanol in useful quantities. The inventors know of no prior art which discloses the successful combination of genes from different organisms, under different control systems, into an operon under a common control system.

BRIEF SUMMARY OF THE INVENTION

The invention described here concerns the construction of a unique portable operon for ethanol production which includes both the alcohol dehydrogenase II and pyruvate decarboxylase activities of the ethanologenic pathway. This unique operon, designated the pet operon, contains the two genes needed for ethanol production. This system is capable of effectively diverting pyruvate to ethanol during growth under both aerobic and anaerobic conditions.

Also described here are novel strains of *E. coli* which contain ethanol-producing operons. These recombinant strains demonstrate the surprising and advantageous characteristic of forming larger colonies on plates containing sugars. Also, these recombinant strains grow to seven-fold higher cell densities in batch culture. Thus, the invention described here can be used to increase the growth and yield of recombinant microorganisms producing any product.

DETAILED DESCRIPTION OF THE INVENTION

Certain bacteria and other simple organisms are capable of actively metabolizing a wide variety of substrates, including hexoses, pentoses, and lactose. This is one of the reasons why *E. coli* is an attractive host for recombinant DNA procedures. The invention described here allows the use of recombinant strains of simple organisms for the production of ethanol from under-utilized sources of biomass, such as hemicellulose (xylose, arabinose, etc.), which represents a major portion of wood and inedible plant parts, and whey (lactose), as well as from other biomass sources. Also, organisms with special capabilities, such as extracellular enzymes for the degradation of complex polymers, can be converted to ethanol producers by using the subject invention.

The novel invention described here can be used in connection with many different hosts. For example, in addition to *E. coli*, enteric bacteria such as *Erwinia chrysanthemi* and *Klebsiella planticola* are particularly attractive hosts because they are capable of utilizing a wide variety of sugars including pentoses and lactose. Additional potential hosts include other bacteria, yeasts, fungi, and eukaryotic cells. Appropriate expression systems would be used for the particular host involved. Ascertaining the proper expression system is within the skill of scientists trained in this field.

Described here is a novel operon which directs cells to produce ethanol. This operon has been designated as the pet operon. The pet operon comprises *Z. mobilis* genes coding for the alcohol dehydrogenase II and pyruvate decarboxylase activities together with appropriate regulatory sequences. The regulatory sequences may consist of promoters, inducers, operators, ribosomal binding sites, terminators, and/or other regulatory sequences. Ethanol production in previous recombinant systems was dependent upon native activities in the host organisms. Advantageously, the dependence upon host alcohol dehydrogenase activity has been eliminated by combining *Z. mobilis* genes encoding alcohol dehydrogenase II and pyruvate decarboxylase to form the PET operon.

Using the materials and methods described herein, significant amounts of ethanol can be produced in recombinants containing the pet operon under both aerobic and anaerobic conditions.

From the foregoing discussion it should be readily apparent to one skilled in the art that the concept disclosed here, i.e., combining genes coding for a metabolic pathway into a single operon, is an extremely novel and useful approach. The application of this concept to a variety of situations where genes from different genetic loci are combined to create a useful operon is envisioned as part of this invention. The creation of the pet operon is only one example of this novel inventive concept. Thus, using the principles described here, genes coding for alcohol dehydrogenase activity from a variety of organisms could be combined with other genes coding for the pyruvate decarboxylase activity in order to create an operon coding for the desired pathway. Operons coding for other pathways could also be created. It should also be apparent to one skilled in the art that, for the ethanolic pathway described here, it is not necessary that the genes coding for alcohol dehydrogenase and pyruvate decarboxylase activities be under common control; they could be under separate control and even in different plasmids, or placed on the chromosome.

Under aerobic conditions in *E. coli*, pyruvate from glycolysis is primarily metabolized by the pyruvate dehydrogenase complex and by lactate dehydrogenase (Gottschalk, G. [1986] *Bacterial Metabolism*, pp. 210-280. Springer-Verlag, New York), with excess acetyl coenzyme A being converted to acetate. The apparent $K_m$s for these two enzymes are 0.4 and 7.2 mM, respectively. The apparent $K_m$ for *Z. mobilis* pyruvate decarboxylase is equal to (pyruvate dehydrogenase) or lower than (lactate dehydrogenase) those for the two *E. coli* enzymes, thereby facilitating acetaldehyde production. NADH+ regeneration under aerobic conditions results primarily from biosynthesis and from the NADH oxidase (coupled to the electron transport system) with an apparent $K_m$ of 50 uM. The apparent $K_m$ for *Z. mobilis* alcohol dehydrogenase II is over fourfold lower than that for *E. coli* NAD+ oxidase, allowing the *Z. mobilis* enzyme to compete effectively for endogenous pools of NADH for the reduction of acetaldehyde to ethanol. Thus, the properties of the *Z. mobilis* ethanologenic enzymes and their relatively high levels of expression are well suited for the diversion of carbon flow into ethanol under aerobic conditions.

Under anaerobic conditions in *E. coli*, pyruvate from glycolysis is primarily metabolized by lactate dehydrogenase and pyruvate formate lyase. The apparent $K_m$s for these two enzymes are 18-fold and 5-fold higher, respectively, than that for *Z. mobilis* pyruvate decarboxylase. Similarly, the apparent $K_m$s for the principal enzymes involved in NAD+ regeneration in *E. coli* are also considerably higher than those for *Z. mobilis* alcohol dehydrogenase II. Thus, the ethanologenic enzymes from *Z. mobilis* are quite competitive for carbon (pyruvate) and reducing potential (NADH) with the normal fermentative enzymes of *E. coli*, allowing the efficient channeling of glycolytic products into ethanol.

The genes encoding the two ethanologenic enzymes, denoted the pet operon, were expressed at high levels and dominated carbon flow from pyruvate and NADH oxidation during anaerobic growth. Under these conditions, the flow of pyruvate carbon skeletons was diverted from the production of organic acids to the production of ethanol as the principal fermentation product in *E. coli*.

The accumulation of organic acids from sugar metabolism is generally regarded as a consequence of fermentation during anaerobic growth. However, appreciable quantities of acetate are produced by the parent strain of *E. coli* TC4 even during rapid agitation under aerobic conditions. The production of acetate by strain TC4 is progressive from the earliest stages of growth and is not limited to the later stages, when cell density is high. This acid production from glucose even under aerobic conditions serves to limit growth in broth and on solid medium, as demonstrated by the increased final cell density in medium supplemented with phosphate buffer.

The conversion of a host organism to ethanolic fermentation can be used to enhance the production of a variety of recombinant products using the host's expression system. The maintenance of function in these products is related to the pH of the broth during growth in dense culture. The extent of this acidification per unit of cell protein is minimized by the production of ethanol rather than of organic acids. Oxygen transfer is frequently a major limitation during the growth of dense cultures of microorganisms, and it is this limitation which results in acid production and pH drift of the growth medium. In recombinants expressing the pet operon, the ethanologenic enzymes of *Z. mobilis* divert part of the pyruvate from glycolysis to acetaldehyde and reoxidize NADH to produce ethanol, a less damaging product of metabolism. Strains containing both functional respiratory chains for oxidative phosphorylation and ethanol production enzymes can be grown to even higher cell densities because of the operation of both systems during the regeneration of NAD+ and a reduction in acidic waste products. Such inherent flexibility results in less stringent process-control requirements, as well as increased yields of recombinant products.

Specifically, the subject invention further concerns the discovery that lactose and all of the major sugars (glucose, xylose, arabinose, galactose, and mannose) present in cellulose and hemicellulose could be converted to ethanol by recombinant *Escherichia coli* containing plasmid-borne genes encoding the enzymes for the ethanol pathway from *Zymomonas mobilis*. Environmental tolerances, plasmid stability, expression of *Z. mobilis* pyruvate decarboxylase, substrate range, and ethanol production (glucose, lactose, and xylose) were compared among 8 strains of *E. coli*. From these 8 strains, *E. coli* ATCC 9637 (pLOI297), ATCC 11303 (pLOI297) and ATCC 15244 (pLOI297) were selected for further development based upon environmental hardiness and ethanol production. Volumetric ethanol productivities per hour in batch culture were found to be approximately 1.4 g ethanol/liter for glucose (12%), 1.3 g/liter for lactose (12%), and 0.64 g/liter for xylose (8%). Ethanol productivities per hour ranged from 2.1 g ethanol/g cell dry weight with 12% glucose to 1.3 g ethanol/g cell dry weight with 8% xylose. The ethanol yield per gram of xylose was higher for recombinant *E. coli* than commonly reported for *Saccharomyces cerevisiae* with glucose. Glucose (12%), lactose (12%), and xylose (8%) were converted to 7.2% ethanol (by vol.), 6.5% ethanol, and 5.2% ethanol, respectively.

A variety of factors need to be considered in selecting *E. coli* strains suitable for ethanol production including substrate range and environmental hardiness (sugar tolerance, salt tolerance, ethanol tolerance, tolerance to low pH, and thermal tolerance). As described herein, strain ATCC 9637 (Waksman strain W) displays superior characteristics in terms of environmental hardiness, although ethanol production from glucose was lower than with other strains. Strain ATCC 9637 was selected primarily for its unique ability to utilize sucrose. Advantageously, this characteristic of ATCC 9637 makes this strain useful in the fermentation of beet sugar, cane sugar, and other feedstocks with sucrose. ATCC 11303 (Luria strain B) and ATCC 15244 (Kepes strain ML300) containing pLOI297 produced the highest levels of ethanol and exhibited acceptable levels of environmental hardiness. Plasmids were quite stable in these two constructs and they were selected as the best candidates for further development of ethanol production. Both constructs expressed the high levels of *Z. mobilis* pyruvate decarboxylase which are required for efficient ethanol production (Ingram et al. [1987] Appl. Environ. Microbiol. 53, supra).

All major sugar components of plant biomass were converted to ethanol by recombinant *E. coli* containing the ethanol pathway from *Z. mobilis*. The conversion efficiency of glucose and xylose into ethanol exceeded that which has been previously reported for *S. cerevisiae*

(Lovitt, R. W., B. H. Kin, G.-J. Shen, and J. G. Zeikus [1988] CRC Crit. Rev. Biotechnol. 7:107-186) and pentose-fermenting yeasts systems (Beck, M. J. [1989] Biotechnol. Bioengin. Symp. 17:617-627; Jeffries, T. W., and H. K. Sreenath [1988] Biotechnol. Bioeng. 31:502-506; Skoog, K., and B. Hahn-Hagerdal [1988] Enzyme Microbiol. Technol. 10:66-79; Slininger, P. J., R. J. Bothast, M. R. Okos, and M. R. Ladisch [1985] Biotechnol. Lett. 7:431-436). Xylose was converted to ethanol by recombinant E. coli with a higher efficiency than glucose by S. cerevisiae (Lovitt et al., supra). The unusually high ethanol yields with xylose (over 100% of theoretical) may include ethanol derived from the catabolism of complex nutrients. Many amino acids and complex medium components are catabolized to glycolytic intermediates which are converted to pyruvate. This pyruvate could then be converted to ethanol.

This work demonstrates that recombinants can be developed for commercial ethanol production, and it illustrates the feasibility of drastic changes in metabolic flow for the future development of novel products from microorganisms. In addition, strains containing the pet operon grow to higher cell densities than do the parent organisms under anaerobic conditions with glucose and offer the potential for the increased production of recombinant products in microorganisms while reducing complications associated with acid production.

MATERIALS AND METHODS

Organisms and growth conditions. E. coli TC4 (Conway, T., Y. A. Osman, J. I. Konnan, E. M. Hoffmann, and L. O. Ingram [1987] "Promoter and nucleotide sequences of the Zymomonas mobilis pyruvate decarboxylase," J. Bacteriol. 169:949-954) and plasmid-containing derivatives were used in the present study. Plasmids containing the pyruvate decarboxylase gene (pLOI276) and the alcohol dehydrogenase B gene (pLOI284) have been described previously (Conway and Osman et al. [1987], "Promoter and nucleotide sequences...," supra; Conway, T., G. W. Sewell, Y. A. Osman, and L. O. Ingram [1987] "Cloning and sequencing of the alcohol dehydrogenase II gene from Zymomonas mobilis," J. Bacteriol. 169:2591-2597).

Strains and growth conditions. Plasmids pUC18 and pUC19 (Yanisch-Perron, C., J. Vieira, and J. Messing [1985] "Improved M13 phage cloning vectors and host strains: nucleotide sequence of the M13mp18 and pUC19 vectors," Gene 33:103-119), pLOI204 (Conway, T., M. O.-K. Byung, and L. O. Ingram [1987] "Expression vector for Zymomonas mobilis," Appl. Environ. Microbiol. 53:235-241), and pLOI295 (Ingram et al. [1987], supra) have been previously described. The construction and properties of pLOI292, pLOI291, pLOI297, pLOI308, pLOI308-2, pLOI308-5, and pLOI308-10 are described below.

Cultures were grown at 37° C. in Luria broth (Luria, S. E. and M. Delbruck [1943] "Mutations of bacteria from virus sensitivity to virus resistance," Genetics 28:491-511) containing 50 g of glucose per liter. Cells for enzyme analyses and inocula for fermentation studies were grown in tubes (13 by 100 mm) containing 3 ml of broth at 37° C. in a tube rotator. Overnight cultures were diluted 100-fold into fresh medium. Aerobic cultures (50 ml of broth in 250 ml flasks) were shaken in a reciprocating water bath (120 oscillations per min). Anaerobic cultures were grown in stoppered serum bottles (100 ml of broth in 130 ml bottles) with gyratary agitation (150 rpm) in a 37° C. incubator. Anaerobic cultures were vented with a 25-gauge needle to allow escape of gaseous fermentation products.

Growth was monitored spectrophotometrically with a Spectronic 70 spectrophotometer (Bausch & Lomb, Inc., Rochester, N.Y.) at 550 nm. Disposable culture tubes (10 by 75 mm) were used as cuvettes. One absorbance unit under our conditions contained approximately 0.25 mg of cellular protein per ml. Growth was measured at $A_{550}$; 1.0 absorbance unit is equivalent to 0.25 mg of total cell protein per ml.

E. coli hosts containing the plasmids of the subject invention were deposited with the American Type Culture Collection (ATCC), 12301 Parklawn Drive, Rockville, Md. 20852 U.S.A. The accession numbers and deposit dates are as follows:

| Culture | Accession number | Deposit date |
|---|---|---|
| E. coli pLOI308-10 | ATCC 67983 | May 15, 1989 |
| TC4(pLOI292) | ATCC 68237 | February 23,1990 |
| TC4(pLOI308-11) | ATCC 68238 | February 23,1990 |
| TC4(pLOI297) | ATCC 68239 | February 23, 1990 |
| TC4(pLOI295) | ATCC 68240 | February 23, 1990 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Genetic techniques. Transformations, plasmid constructions, DNA digestions, and analyses were carried out as previously described. Recombinants were selected on solid media (1.5% agar) containing 2 g of glucose per liter and appropriate antibiotics. Recombinants containing functional ethanologenic genes from Z. mobilis were identified by their growth as oversized colonies on Luria agar plates containing glucose and were confirmed by their poor growth on Luria agar plates lacking glucose and by the expression of alcohol dehydrogenase on aldehyde indicator medium.

Enzyme assays. Cells were disrupted, heat-inactivated, and assayed for pyruvate decarboxylase activity (thermostable) as described previously (Conway and Osman et al. [1987] "Promoter and nucleotide sequences...," supra). Cells were prepared and assayed for alcohol dehydrogenase II activity in the direction of ethanol oxidation as described previously, except that cells were washed and disrupted in 30 mM potassium phosphate buffer to which solid ferrous ammonium sulfate (final concentration, 0.5 mM) and sodium ascorbate (10 mM) had been freshly added as described by Neale et al. (Neale, A. D., R. K. Scopes, J. M. Kelly, and R. E. H. Wettenhall [1986] "The two alcohol dehydrogenases of Zymomonas mobilis: purification by differential dye ligand chromatography, molecular characterization and physiological role," Eur. J. Biochem. 154:119-124). This modification coupled with the immediate assaying of alcohol dehydrogenase activity without storage resulted in a much higher specific activity than that previously reported. Protein was measured with the Folin phenol reagent (Lowry, O. H., N. J. Rosebrough, A. L. Farr, and R. J. Randall [1951] "Protein measurement with the Folin phenol reagent," J. Biol. Chem. 193:265-275).

Analysis of fermentation products. Fermentation products were determined in clarified broth with a Millipore/Waters high-performance liquid chromatograph (Millipore Corp., Bedford, Mass.) equipped with a refractive index monitor and an electronic integrator. Separations were performed on an Aminex HPX-87H column (300 by 7.8 mm) purchased from Bio-Rad Laboratories, Richmond, Calif., at 65° C. at a flow rate of 0.25 ml/min (100 μl injection volume). Peaks were identified by using authentic standards. The two peaks eluting before glucose and the later unknown peak eluting at 45.4 to 45.8 min are components of uninoculated medium.

Following are examples which illustrate procedures, including the best mode, for practicing the invention. These examples should not be construed as limiting. All percentages are by weight and all solvent mixture proportions are by volume unless otherwise noted.

EXAMPLE 1

Strain Construction

Figure 1:
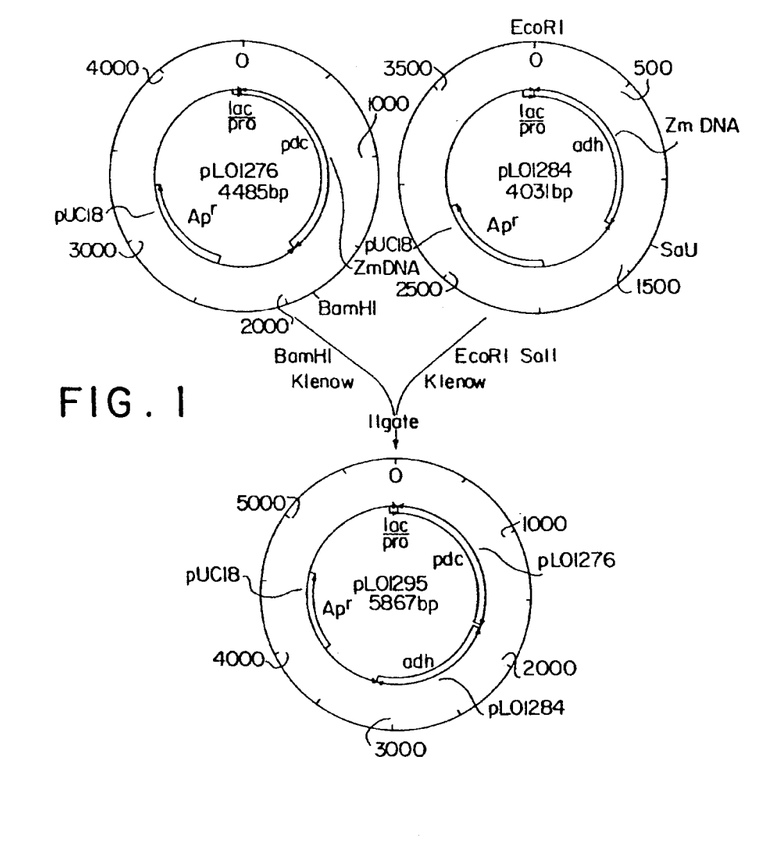
FIG. 1 shows the construction of pLOI295 containing genes encoding pyruvate decarboxylase and alcohol dehydrogenase II from *Zymomonas mobilis.*
Figure 2:
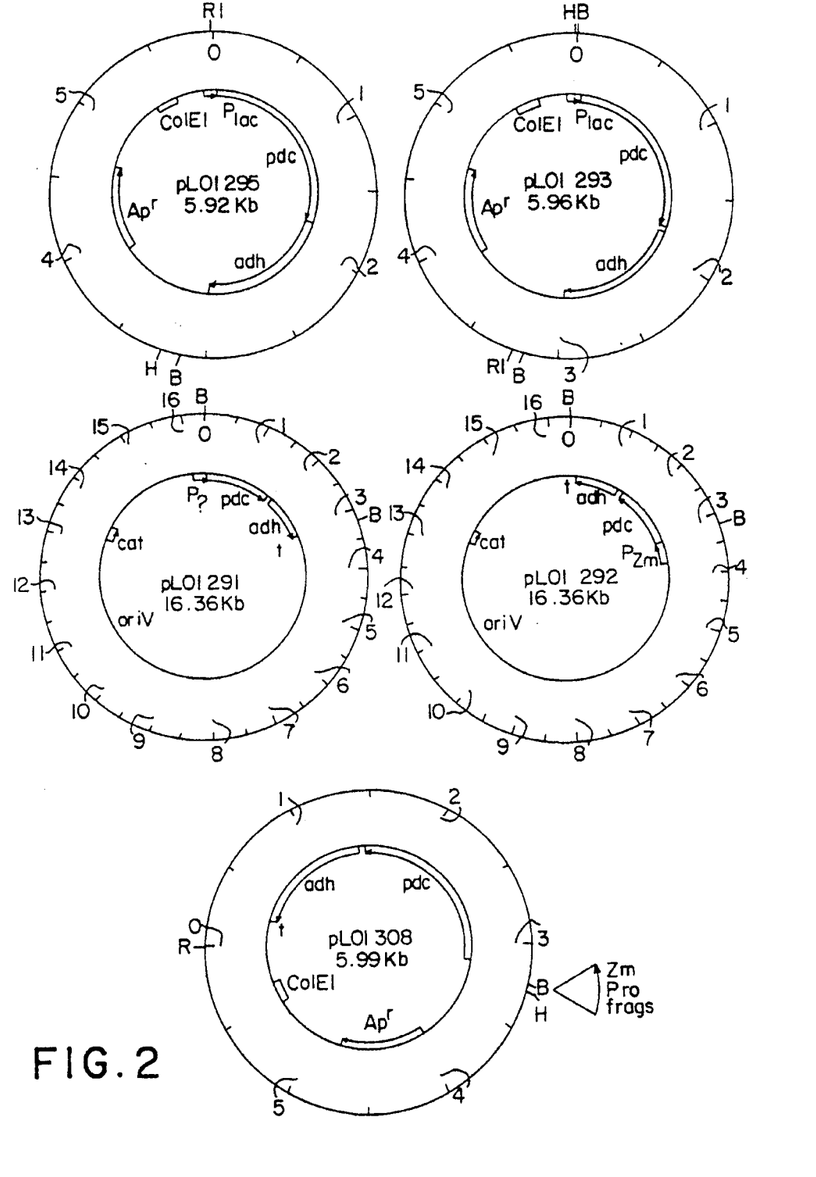
FIG. 2 shows several plasmids containing the genes encoding pyruvate decarboxylase and alcohol dehydrogenase II from *Zymomonas mobilis.* Abbreviations used in FIG. 2 are as follows: RI, *Eco*RI; H, *Hin*dIII; B, *Bam*HI; t, terminator; adh, *Z. mobilis* alcohol dehydrogenase II; pdc, *Z. mobilis* pyruvate decarboxylase; cat, chloramphenicol acyltransferase; Ap, β-lactamase; Zm Pro frags, fragments of *Z. mobilis* which exhibit promoter activity; ColE1, replication origin derived from pBR322; oriV, replication origin derived from RSF1010; P$_{lac}$, *lac* promoter; P$_{zm}$, promoter from *Z. mobilis*; P?, cryptic promoter on vector; Kb, kilobases.

The sizes of the structural genes coding for pyruvate decarboxylase and alcohol dehydrogenase II are 1.7 and 1.1 kilobases, respectively, and these genes encode proteins with molecular weights of 60,000 and 40,100. These genes are each located on derivatives of pUC18 under the control of the lac promoter (FIG 1). The two genes are combined by inserting the promoterless 1.4 kilobase fragment generated by restriction endonucleases EcoRI and SalI from pLOI284 (alcohol dehydrogenase) into the BamHI site downstream from the pyruvate decarboxylase gene in pLOI276. These clones were selected for resistance to ampicillin and for the presence and expression of alcohol dehydrogenase activity on a newly developed pararosaniline-ethanol indicator plate which detects the production of aldehydes. Clones containing the indicated construction, pLOI295, grew poorly on the surface of Luria agar plates (aerobic) in the absence of added glucose but grew to much higher densities than the plasmid-free strain and strains containing pLOI276 or pLOI284 on agar plates containing 2% glucose.

Recombinants containing the pet operon were readily detected as larger, more opaque colonies on Luria agar plates (aerobic) containing glucose. This difference in colony size and opacity has proven to be a useful marker for the identification of recombinants which contain plasmids expressing both alcohol dehydrogenase and pyruvate decarboxylate genes.

The complete base sequence of pLOI295 is known. The open reading frame for the gene coding for pyruvate decarboxylase begins 163 bases downstream from the lac promoter and ends with two stop codons 85 bases upstream from the open reading frame of the gene coding for alcohol dehydrogenase II. Both genes include sequences which resemble ribosome-binding sites immediately upstream from each open reading frame. The gene encoding alcohol dehydrogenase II contains a single stop codon followed by a palindromic sequence of 13 base pairs which serves as a transcriptional terminator.

EXAMPLE 2

Expression of Z. mobilis Genes in E. coli

Both pyruvate decarboxylase and alcohol dehydrogenase II genes were expressed at high levels in E. coli under the control of the lac promoter singly (pLOI276 and pLOI284, respectively) and jointly. Pyruvate decarboxylase is not present in wild-type E. coli, but an inducible alcohol dehydrogenase is present at low concentrations. During growth of E. coli in the presence of glucose, the specific activities of the Z. mobilis enzymes declined by approximately 50%, which is consistent with glucose repression of the lac promoter. The specific activity of pyruvate decarboxylase, coded for by the proximal gene in the pet operon, was threefold higher in pLOI295 than in pLOI276. The specific activity of the product of the alcohol dehydrogenase II gene, the distal gene in the pet operon, was expressed in pLOI295 at twice the level in pLOI284.

EXAMPLE 3

Fermentation of Glucose by Recombinant Strains

Figure 3A:
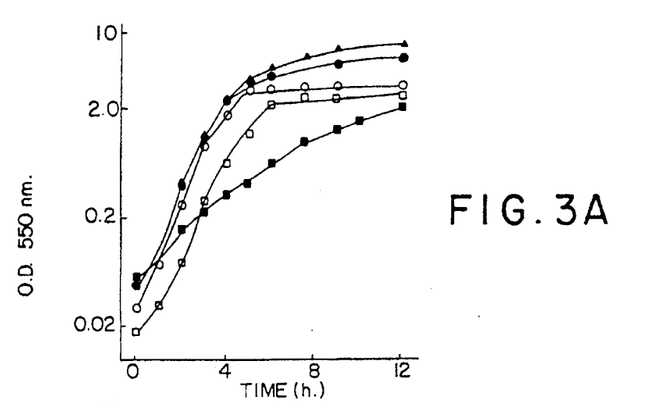
FIG. 3 shows growth and acid production by strain TC4 and recombinants containing plasmids encoding ethanologenic enzymes.
Figure 3B:
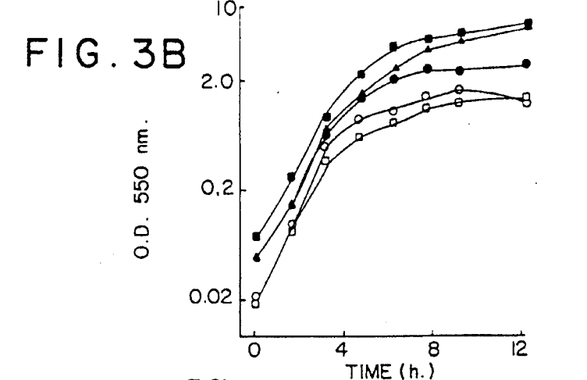
Figure 3C:
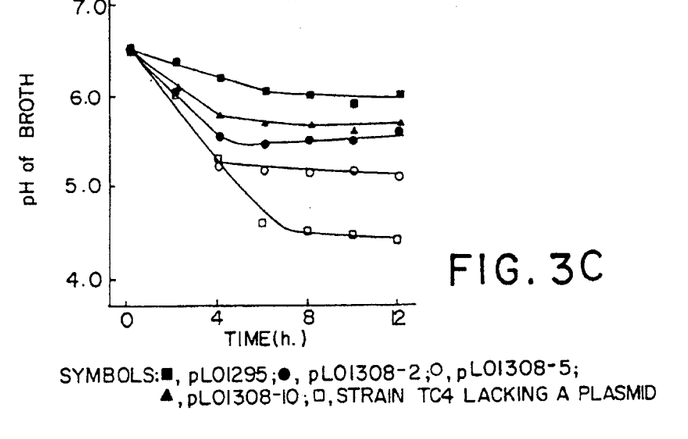

Expression of the pet operon in E. coli resulted in the production of ethanol as the primary fermentation product during anaerobic growth. The parent strain produced succinate (1.5 mM), lactate (18 mM), and acetate (7 mM) as major fermentation products (FIG. 3A). An identical fermentation profile was observed in cells containing pLOI284, which carries the alcohol dehydrogenase II gene (FIG. 3C). With pLOI276 carrying the gene coding for pyruvate decarboxylase, an ethanol peak is clearly evident (18 mM), equivalent to one-third of the accumulated fermentation products. This higher level of ethanol results from the combined activities of the pyruvate decarboxylase from Z. mobilis and the native E. coli alcohol dehydrogenase. With pLOI295 containing the pet operon (both pyruvate decarboxylase and alcohol dehydrogenase II genes from Z. mobilis), E. coli produced large amounts of ethanol (750 mM; 4.3%, vol/vol), which represented over 95% of the fermentation products.

The high levels of alcohol dehydrogenase and pyruvate decarboxylase produced in cells containing the pet operon dominated NADH oxidation in E. coli. Thus, the fermentation of this organism was converted to the equivalent of those of S. cerevisiae and Z. mobilis. During normal fermentative growth, pyruvate is converted to acetyl coenzyme A by the pyruvate dehydrogenase complex, to oxaloacetate (and on to succinate) by phosphoenolpyruvate carboxylase, to formate and acetyl coenzyme by pyruvate formate lyase, and to lactate by lactate dehydrogenase. This last pathway is the dominant route for the regeneration of $NAD^+$ in unmodified strains of *E. coli*. However, the $K_m$s for bacterial lactate dehydrogenases are quite high, ranging from 10 to 1,000 mM (Garvie, E. I. [1980] "Bacterial lactate dehydrogenases," Microbiol. Rev. 44:106–139; Tarmy, E. M., and N. O. Kaplan [1968] "Kinetics of *Escherichia coli* B D-lactate dehydrogenase and evidence for pyruvate controlled change in conformation," J. Biol. Chem. 243:2587–2596). The $K_m$ of the pyruvate decarboxylase from *Z. mobilis* is 0.4 mM (Bringer-Meyer, S., K.-L. Schimz, and H. Sahm [1986] "Pyruvate decarboxylase from *Zymomonas mobilis*: Isolation and partial characterization," Arch. Microbiol. 146:105–110). The abundance of this enzyme, coupled with the lower $K_m$, effectively diverts the flow of pyruvate from glycolysis into ethanol.

High cell densities are also achieved during mixed growth conditions with moderate agitation or stirring of culture vessels in which gas exchange is not restricted. Under these conditions, a final pH of 6.3 or above was observed, depending upon the extent of aeration.

EXAMPLE 4

Plasmid Constructions and Expression of *Z. mobilis* Ethanologenic Enzymes in *E. coli*

Plasmid pLOI295 contains the *Z. mobilis* genes encoding pyruvate decarboxylase and alcohol dehydrogenase II under the control of the *lac* promoter. This construction is referred to as the pet operon and used as the source of ethanologenic genes for the construction of additional plasmids with alternative promoters. The *Eco*RI-*Sal*I fragment from pLOI295 containing the ethanologenic genes was treated with the Klenow fragment of DNA polymerase to produce blunt ends. This blunt-ended DNA fragment was inserted into the *Sma*I site of pUC19 with the pdc gene immediately downstream from the *lac* promoter. The resulting plasmid, denoted pLOI293, contained the pet genes flanked by *Bam*HI sites. Plasmids pLOI291 and pLOI292 (opposite orientations) were constructed by inserting the *Bam*HI fragment containing the genes encoding the ethanologenic enzymes into the expression vector pLOI204. The *Bam*HI fragment includes the ribosome-binding site, complete sequences for both genes, and a stem-loop terminator distal to *adh*B. In pLOI292, the two genes are expressed under the control of the *Z. mobilis* promoter contained in the original expression vector.

Plasmid pLOI308 was constructed to remove the pet genes from the control of the *lac* promoter but to retain the upstream *Bam*HI site for the insertion of alternative promoters. Partial digestion of pLOI293 with *Bam*HI and Klenow treatment were used to remove the *Bam*HI site distal to the *adh*B gene. The ethanologenic genes were removed from this plasmid as a promoterless *Bam*HI (immediately proximal to pdc)-*Eco*RI (distal to *adh*B) fragment, which was directionally inserted into the *Bam*HI and *Eco*RI sites of pUC18 to produce pLOI308. This plasmid expressed low levels of *adh*B on aldehyde indicator plates but did not exhibit the large-colony phenotype associated with the other functional pet plasmids pLOI295, pLOI291, and pLOI292.

Chromosomal DNA from *Z. mobilis* was partially digested with *Sau*3A such that most of the DNA appeared to be less than 4 kilobases long. This unfractionated DNA was used as a source of promoter fragments and was ligated into the dephosphorylated *Bam*HI site of pLOI308. Ampicillin-resistant recombinants with a well-expressed pet operon were identified as large colonies on Luria agar plates containing glucose. Three of the recombinant strains, pLOI308-2, pLOI308-5, and pLOI308-10, were selected for study. The *Z. mobilis* DNA fragments with promoter activity in these plasmids were 6, 2, and 2 kilobases long, respectively.

Table 1 summarizes the activities of pyruvate decarboxylase and alcohol dehydrogenase in overnight cultures of the recombinant *E. coli*. The activities of pyruvate decarboxylase ranged from 0.37 IU/mg of cell protein in strain TC4(pLOI291) to 8.23 IU in TC4(pLOI295). In terms of pyruvate decarboxylase activity, the recombinant strains of TC4 can be ordered as follows (highest to lowest): pLOI295 > pLOI308-10 > pLOI308-2 > pLOI308-5 > pLOI292 > pLOI291.

TABLE 1

Expression of ethanologenic enzymes from *Z. mobilis* in *E. coli*

| Plasmid | Pyruvate decarboxylase | | Alcohol dehydrogenase | |
|---|---|---|---|---|
| | Sp act[a] | % Cell protein[b] | Sp act[a] | % Cell protein[c] |
| pLOI291 | 0.37 | 0.4 | 0.21 | 0.02 |
| pLOI292 | 0.48 | 0.5 | 0.30 | 0.03 |
| pLOI308-2 | 2.26 | 2.3 | 1.54 | 0.21 |
| pLOI308-5 | 1.11 | 1.1 | 0.76 | 0.10 |
| pLOI308-10 | 6.5 | 6.5 | 2.51 | 0.34 |
| pLOI295 | 8.2 | 8.2 | 9.65 | 1.4 |
| None | 0 | 0 | 0.08 | |

[a]Expressed as micromolecules of substrate utilized per minute per milligram of total cellular protein.
[b]Calculated assuming a specific activity of 100 for the pure enzyme.
[c]Calculated assuming a specific activity of 710 for the pure enzyme after subtraction of native alcohol dehydrogenase activity.

Alcohol dehydrogenase activities in the recombinant strains followed the same trend in terms of expression from different plasmids as did pyruvate decarboxylase. The alcohol dehydrogenase activities measured represent a combination of the native enzyme from *E. coli* and the *Z. mobilis* enzyme. The level observed in strain TC4 lacking a plasmid was relatively small in comparison to those observed in strains carrying plasmids with the *Z. mobilis* gene. The activities of the *Z. mobilis* enzyme (corrected for native *E. coli* alcohol dehydrogenase) ranged from 0.13 IU/mg of cell protein from strain TC4(pLOI291) to 9.6 IU in TC4(pLOI295).

EXAMPLE 5

Growth of Recombinant Strains Containing the Ethanologenic Enzymes From *Z. mobilis*

Shifting the catabolism of glucose to the production of ethanol also affected growth yield and pH drift of the growth medium. Although fermentation products are relatively nontoxic, they may accumulate to toxic levels during fermentation. During anaerobic growth in bottles containing Luria broth containing 10% glucose, the plasmid-free strain and the strain carrying pLOI284 (carrying the gene coding for alcohol dehydrogenase II) achieved a final density of 0.25 mg of cell protein per ml after 48 hr, with a final pH of 4.4. The cell density increased by twofold in the strain carrying pLOI276 (carrying the gene coding for pyruvate decarboxylase), with a final pH of 4.5. The final cell density of the strain carrying pLOI295 (pet operon) was 2.5 mg/ml, 10-fold higher than that of the control strain. The final pH was 4.7. At a density of 2.5 mg of cell protein per ml, magnesium appears to be limiting, and a 1.5-fold further increase in cell density is readily achieved by the addition of 0.5 mM magnesium sulfate.

The growth of the recombinant strains was examined under both aerobic and anaerobic conditions (FIG. 3). Under aerobic conditions (FIG. 3A and Table 2), strain TC4 grew with a generation time of approximately 30 min during the most rapid phase of growth. Strain TC4 carrying the derivatives of pLOI308 exhibited equivalent maximal rates of growth, with generation times between 26 and 30 min. Strain TC4(pLOI295) grew poorly under these conditions (generation time, 71 min) and was accompanied by partial lysis. Strains TC4(pLOI291) and TC4(pLOI292) grew at intermediate rates, each with a generation time of 46 min.

TABLE 2

Maximal generation times, final cell densities, and final pHs of the broth during aerobic and anaerobic growth.

| Growth Condition | Plasmid | Cell density$^a$ (mg of protein/ml) | Generation time (min) | Final pH$^a$ |
|---|---|---|---|---|
| Aerobic | None | 0.7 | 29 | 4.4 |
| | pLOI291 | 0.7 | 46 | 5.3 |
| | pLOI292 | 1.3 | 46 | 5.1 |
| | pLOI295 | 1.1 | 71 | 5.7 |
| | pLOI308-2 | 1.7 | 27 | 5.5 |
| | pLOI308-5 | 0.8 | 30 | 5.0 |
| | pLOI308-10 | 2.5 | 26 | 5.0 |
| Anaerobic | None | 0.3 | 32 | 4.4 |
| | pLOI291 | 0.4 | 40 | 4.5 |
| | pLOI292 | 1.0 | 48 | 5.0 |
| | pLOI295 | 2.1 | 39 | 4.7 |
| | pLOI308-2 | 0.8 | 42 | 5.7 |
| | pLOI308-5 | 0.4 | 38 | 4.9 |
| | pLOI308-10 | 2.2 | 41 | 5.2 |

$^a$Measured after 24 hr of growth.

Under anaerobic conditions (FIG. 3B and Table 2), the generation time for strain TC4 lacking a plasmid was 32 min, considerably shorter than that for the recombinant strains containing the ethanologenic enzymes. All of the recombinants exhibited similar maximal rates of growth, with generation times between 38 and 41 min, except for TC4(pLOI292), which grew somewhat more slowly, with a generation time of 48 min.

All of the recombinants except TC4(pLOI295) grew after 12 hr under anaerobic and aerobic growth conditions to cell densities equivalent to or higher than those of strain TC4 lacking a plasmid (FIGS. 3A and B). Table 2 summarizes the final cell densities of strain TC4 and the recombinants after 24 hr of growth. Under aerobic conditions, strain TC4 containing pLOI308-10 reached the highest cell density, followed by TC4 containing pLOI308-2, pLOI292, pLOI295 (with some lysis apparent), and pLOI308-5.

Under anaerobic conditions, the final cell densities of strain TC4 containing pLOI308-10 and pLOI295 were roughly equivalent, followed by those of TC4 containing pLOI292, pLOI308-2, pLOI308-5, and pLOI291.

Figure 4:
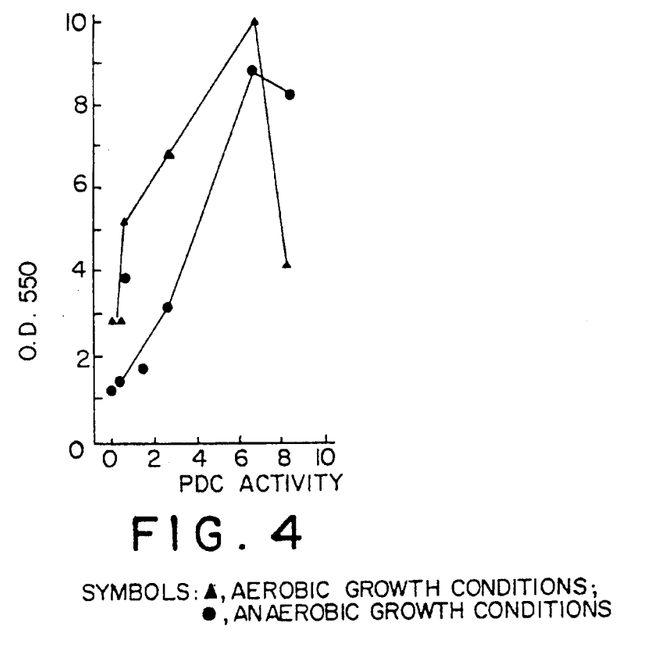
FIG. 4 shows the relationship between pyruvate decarboxylase activity in recombinants and the extent of growth. Cell mass after 24 hours of growth is expressed as the optical density at 550 nm (O.D. 550).

FIG. 4 shows the relationship between the level of pyruvate decarboxylase activity in cells and the final cell density after 24 hr of growth. Since the synthesis of pyruvate decarboxylase is coupled to that of alcohol dehydrogenase II in these recombinants, this plot represents the effects of the alternative Z. mobilis system for NAD+ regeneration on final cell density. From these data, it is clear that the expression of the Z. mobilis pathway for the production of ethanol increases final cell density under both anaerobic and aerobic conditions. In strain TC4(pLOI308-10), the levels of expression of pyruvate decarboxylase (6.5 IU) and alcohol dehydrogenase II (2.5 IU) were nearly optimal for both anaerobic and aerobic growth. The level of expression of ethanologenic enzymes in strain TC4(pLOI295) appears to be excessive, resulting in diminished cell growth accompanied by partial lysis under aerobic conditions and slightly reduced growth under anaerobic conditions.

The increased growth of strain TC4(pLOI295) under anaerobic conditions with little apparent lysis in contrast to the poor growth and lysis during growth in rapidly shaken flasks suggested that a highly aerobic environment may be damaging to this construction. Lysis in this recombinant was dramatically reduced and the final cell density was increased during growth in shaken flasks when the speed of oscillation was decreased by one-third.

EXAMPLE 6

Effects of Ethanologenic Enzymes on the Acidification of Broth During Growth

FIG. 3C shows a plot of the changes in the pH of the broth during anaerobic growth. The pH fell rapidly during the first 6 hr of growth of strain TC4 lacking a plasmid but declined more slowly in derivatives containing the ethanologenic enzymes. Acidification during the initial 12 hr was reduced to the greatest extent in strain TC4 containing pLOI295, followed by TC4 containing pLOI308-10, pLOI308-2, and pLOI308-5. Data for strains TC4(pLOI291) and TC4(pLOI292) are not shown but lie below and above those for TC4(pLOI308-5), respectively. Although the recombinants reached a higher final cell density, the pH of the broth from the recombinants grown under both anaerobic and aerobic conditions for 24 hr was less acidic than that of the broth from strain TC4 lacking ethanologenic enzymes (Table 2).

The reduced rate and extent of acidification in recombinants accompanied by increased cell growth suggested that the fall in pH was a major factor limiting growth even under highly aerobic conditions. This hypothesis was supported by an 85% increase in the final cell density of strain TC4 (lacking a plasmid) grown in medium supplemented with a 1/10 volume of 1M sodium phosphate buffer (pH 7.0). Lower levels of buffer addition resulted in intermediate levels of growth.

EXAMPLE 7

Effects of Ethanologenic Enzymes on Fermentation Products

Table 3 summarizes the analyses of fermentation products made by strain TC4 and the recombinants after 24 hr of growth under aerobic and anaerobic conditions. Under aerobic conditions, acetate was the primary fermentation product that accumulated during the growth of strain TC4 lacking a plasmid in rich medium, with no detectable ethanol. The amount of acetate produced was drastically reduced in strains containing the ethanologenic enzymes from Z. mobilis, and ethanol appeared as the major fermentation product. Strain TC4 containing pLOI308-10 produced the most ethanol, followed by TC4 containing pLOI295, pLOI308-2, pLOI292, pLOI308-5, and pLOI291. Under these aerobic conditions, small amounts of lactate were also produced (0.6 to 1.2 mM) by all of these strains. Only strain TC4 containing pLOI308-10 accumulated appreciable amounts of succinate, although this product still represented only 1% of the total fermentation products, with 94% being ethanol.

TABLE 3

Comparison of fermentation products during aerobic and anaerobic growth

| Growth Condition | Plasmid | Fermentation product [mM (SD)] | | | |
|---|---|---|---|---|---|
| | | Succinate | Lactate | Acetate | Ethanol |
| Aerobic | None | 0.2 (0.1) | 0.6 (0.2) | 55 (2) | Tr |
| | pLOI308-2 | Tr | 1.2 (0.3) | 22 (2) | 98 (3) |
| | pLOI308-5 | Tr | 0.9 (0.2) | 43 (3) | 15 (2) |
| | pLOI308-10 | 4.9 (0.5) | 1.0 (0.2) | 17 (2) | 337 (21) |
| | pLOI295 | Tr | 1.1 (0.4) | 13 (1) | 114 (10) |
| | pLOI291 | Tr | 0.6 (0.2) | 34 (3) | 7 (1) |
| | pLOI292 | Tr | 1.3 (0.2) | 30 (1.5) | 24 (1) |
| Anaerobic | None | 0.9 (0.1) | 22 (1) | 7 (0.3) | 0.4 (0.2) |
| | pLOI308-2 | 0.8 (0.1) | 7 (0.5) | 4 (0.3) | 71 (5) |
| | pLOI308-5 | 0.3 (0.1) | 18 (2) | 6 (1) | 16 (2) |
| | pLOI308-10 | 5.0 (0.4) | 10 (1) | 1.2 (0.2) | 482 (23) |
| | pLOI295 | 2.2 (0.20) | 6 (1) | 3 (0.3) | 90 (2) |
| | pLOI291 | 1.0 (0.1) | 15 (0.5) | 7 (0.2) | 4 (0.5) |
| | pLOI292 | 2.3 (0.2) | 9 (0.7) | 7.2 (0.3) | 21 (1) |

Under anaerobic conditions, lactate was the principal fermentation product that accumulated during 24 hr of growth of strain TC4 lacking a plasmid in rich medium containing glucose, with lesser amounts of acetate, succinate, and ethanol being present. Lactate production was dramatically reduced in strains containing the ethanologenic enzymes and was accompanied by the production of substantial quantities of ethanol. Strain TC4(pLOI308-10) produced the largest amount of ethanol, and this product alone represented 97% of the total soluble fermentation products. The trend of ethanol production among the organisms tested was the same as that during aerobic growth. All organisms except TC4(pLOI308-10) actually produced less total ethanol after 24 hr under anaerobic conditions than under aerobic conditions. It is likely that this lower level of accumulated ethanol was caused by the reduction in total cell mass produced under these anaerobic conditions, thus reducing the volumetric rate of ethanol production.

The extent of ethanol production under anaerobic and aerobic conditions (Table 3) was directly related to the level of expression of the Z. mobilis ethanologenic genes (Table 1). Ethanol production appeared to be optimal in strain TC4(pLOI308-10), with a pyruvate decarboxylase activity of 6 IU and alcohol dehydrogenase II activity of 2.5 IU.

Derivatives of E. coli TC4 containing plasmids which express the ethanologenic enzymes from Z. mobilis grew to higher cell densities than did the parent organism lacking a plasmid. The increase in the final cell density, the extent to which ethanol accumulated in the medium, and the reduction in the rate of acidification of the culture broth during growth all correlated with the level of expression of Z. mobilis ethanologenic enzymes. Heterologous promoters were used to express the genes in all constructions except pLOI295 (lac) to minimize potential problems associated with transcriptional regulation. The level of expression nearest to optimal for growth and ethanol production was provided by pLOI308-10 (6.5 IU of pyruvate decarboxylase and 2.5 IU of alcohol dehydrogenase II per mg of total cellular protein). This level of expression in E. coli is considerably higher than that present in Z. mobilis CP4, which contains only the ethanol pathway for the regeneration of NAD+.

The level of expression of ethanologenic enzymes appeared to be excessive in strain TC4(pLOI295)(approximately 17% of the soluble cellular protein). This high level of expression was accompanied by partial cell lysis, slower growth, and a reduction in ethanol production under aerobic conditions. These effects were reduced by slower agitation and by growth under anaerobic conditions. The apparent damage and partial lysis that occurred during highly aerobic growth may have been related to the depletion of NADH by a combination of the high levels of Z. mobilis alcohol dehydrogenase II and the native NADH oxidase (coupled to the electron transport system).

The production of ethanol as a major product does not appear to adversely affect the growth rate of E. coli TC4. Strains containing derivatives of pLOI308 (ColE1 replicon) expressing the pet operon and producing ethanol grew as rapidly as did the parent organism under aerobic conditions with glucose and reached higher final cell densities than did the parent organism. Strains containing pLOI291 or pLOI292 with the RSF1010 replicon grew more slowly under aerobic conditions. Since these two constructions expressed lower levels of the ethanologenic enzymes and produced less ethanol than did pLOI308-10, the reasons for the slower growth can be attributed to properties of the vector rather than to the expression of the pet operon.

EXAMPLE 8

Preparation of Additional Strains

Additional E. coli strains were tested in order to try and identify bacteria with superior characteristics for use as an ethanol producing microbe. The following E. coli strains were evaluated: ATCC 8677, ATCC 8739, ATCC 9637, ATCC 11303, ATCC 11775, ATCC 14948, ATCC 15244, and ATCC 23227. These were grown in a shaking water bath at 30° C. in Luria broth (Luria, S. E. and M. Delbruck [1943] Genetics 28:491-511) containing tryptone (10 g/liter), yeast extract (5 g/liter), sodium chloride (5 g/liter), and a fermentable sugar. Glucose and lactose were added at concentrations of 100 g/liter and xylose at a concentration of 80 g/liter unless indicated otherwise. Sugars were autoclaved separately (121° C., 15 min), double strength in distilled water. Xylose (Sigma Chemical Co., St. Louis, Mo.) solutions were acidic and were neutralized with sodium hydroxide prior to autoclaving; failure to neutralize resulted in extensive browning and decomposition. Similar fermentation results were obtained with sugars which were autoclaved or filter-sterilized. Survival in broth and on plates of recombinant strains containing genes encoding the enzymes of the ethanol pathway required the presence of a fermentable sugar. Where indicated, tetracycline was added at a final concentration of 10 mg/liter.

EXAMPLE 9

Environmental Hardiness of Additional Strains

Prior to the introduction of plasmids for ethanol production, the growth of the previously-identified 8 different strains of E. coli were compared for environmental hardiness. Strains were tested for their resistance to sodium chloride, sugars, low pH, and ethanol. Concentrations of sodium chloride and sugars in Table 4 include that present in the original medium. The original pH of the medium was 6.8; this was adjusted to lower values with HCl where indicated. Acidified media were sterilized by filtration. Ethanol was added to autoclaved medium after cooling. Sugars were autoclaved separately. Overnight cultures grown in each respective sugar in the absence of test agent were diluted 60-fold into 13×75 mm culture tubes containing 3 ml of test media. Growth was measured as O.D. at 550 nm after 48 hours. An O.D. of 1.0 is equivalent to 0.25 mg/ml of cell protein and 0.33 mg of cell dry weight. In tests of environmental hardiness, a final O.D. below 0.2 reflected less than two doublings and was considered negligible.

Table 4 summarizes these results in medium containing glucose. Similar results were obtained in medium containing lactose or xylose. Strains ATCC 8677, ATCC 8739, and ATCC 11775 were particularly sensitive to inhibition by low concentrations of ethanol. Strains ATCC 9637 and ATCC 11775 were the most resistant to low pH although all strains grew for at least 2 to 4 doublings at pH 4.0 except ATCC 23227. All strains grew at 45° C. with limited growth at higher temperatures; none could be subcultured above 45° C. All strains grew in media containing 20% glucose, 20% lactose, or 12% xylose.

supplemented with 2% carbohydrate were scored positive for sugar utilization (Silhavy, T. J. and J. R. Beckwith [1985] Microbiol. Rev. 49:398–418). Cells were also tested using the Biolog EC plates (Biolog, Inc., Hayward, Calif.) according to the directions of the manufacturer. The Biolog plates were rapid and convenient, detecting NADH production (conversion of a tetrazolium salt to the insoluble formazan) as a measure of substrate utilization. Both methods were in complete agreement for the 13 sugars examined.

All strains tested utilized glucose, fructose, galactose, mannose, arabinose, lactose, glucuronic acid, and galacturonic acid. Strain 11775 did not utilize xylose. Maltose and maltotriose were not used by ATCC 11303 and ATCC 23227. All strains exhibited a weak positive reaction with cellobiose. Only strain ATCC 9637 utilized sucrose. The results of the sugar utilization studies are shown in Table 5.

TABLE 5

| | Growth of *E. coli* strains harboring pLOI297 and pLOI308-11. | | | | | | | | |
|---|---|---|---|---|---|---|---|---|---|
| | | Final O.D. 550 nm of *E. coli* strains (ATCC numbers) | | | | | | | |
| Sugar | Plasmid | 8677 | 8739 | 9637 | 11303 | 11775 | 14948 | 15224 | 23227 |
| Glucose | none | 4.0 | 3.7 | 6.1 | 6.0 | 4.7 | 5.6 | 7.0 | 6.6 |
| Glucose | pLOI297 | 10.0 | 10.5 | 10.5 | 10.0 | 9.5 | — | 9.5 | 10.2 |
| Glucose | pLOI308-11 | 9.8 | 9.5 | 11.4 | 11.2 | — | 9.3 | 10.8 | 11.4 |
| Lactose | none | 4.3 | 3.8 | 7.5 | 6.0 | 4.5 | 6.1 | 7.0 | 6.4 |
| Lactose | pLOI297 | 13.0 | 6.8 | 11.6 | 10.8 | 7.6 | — | 10.5 | 7.0 |
| Lactose | pLOI308-11 | 10.0 | 10.0 | 11.5 | 11.0 | — | 7.3 | 10.0 | 10.0 |
| Xylose | none | 4.1 | 3.7 | 7.7 | 7.3 | 4.9 | 5.9 | 7.2 | 7.0 |
| Xylose | pLOI297 | 8.1 | 10.6 | 10.8 | 10.6 | 4.7 | — | 11.0 | 11.0 |
| Xylose | pLOI308-11 | 10.0 | 6.8 | 11.4 | 8.5 | — | 11.4 | 10.6 | 12.0 |

Dashed lines indicate no data available.

EXAMPLE 11

Genetic Alteration of Additional Strains

Two new plasmids were constructed using standard methods (Maniatis, T., E. F. Fritsch, and J. Sambrook

TABLE 4

| | Growth of *E. coli* in Luria broth containing 100 g/l glucose under chemical and physical stresses. | | | | | | | |
|---|---|---|---|---|---|---|---|---|
| | Growth of *E. coli* strains (ATCC numbers) | | | | | | | |
| Stress | 8677 | 8739 | 9637 | 11303 | 11775 | 14948 | 15224 | 23227 |
| NaCl (g/l) | | | | | | | | |
| 50 | + | ++ | ++ | ++ | ++ | ++ | ++ | ++ |
| 60 | 0 | + | ++ | ++ | + | ++ | + | ++ |
| 70 | 0 | 0 | + | + | 0 | + | + | + |
| Ethanol (% by vol.) | | | | | | | | |
| 3.8 | ++ | ++ | ++ | ++ | ++ | ++ | ++ | ++ |
| 5.0 | ++ | ++ | + | + | + | + | + | + |
| 6.3 | 0 | ++ | + | + | + | + | + | 0 |
| 7.5 | 0 | + | + | 0 | 0 | + | 0 | 0 |
| 8.8 | 0 | 0 | 0 | 0 | 0 | 0 | 0 | 0 |
| Acidity | | | | | | | | |
| pH 4.50 | ++ | ++ | ++ | ++ | ++ | ++ | ++ | ++ |
| pH 4.25 | ++ | ++ | ++ | + | ++ | ++ | ++ | + |
| pH 4.00 | + | + | ++ | + | ++ | + | + | 0 |
| pH 3.75 | 0 | 0 | + | 0 | + | 0 | 0 | 0 |
| Temperature (°C.) | | | | | | | | |
| 45 | ++ | ++ | ++ | ++ | + | ++ | ++ | ++ |
| 47 | + | + | + | + | + | + | + | + |
| 49 | 0 | 0 | + | + | 0 | 0 | + | + |

0 = less than two doublings in O.D. 550 nm
+ = two to four doublings
++ = over four doublings

EXAMPLE 10

Sugar Utilization of Additional Strains

Sugar utilization was tested in two ways. Strains which developed red colonies on MacConkey agar

[1982] *Molecular Cloning: A Laboratory Manual.* Cold Spring Harbor Laboratory, Cold Spring Harbor, N.Y.) which contained resistance genes for ampicillin and tetracycline as selectable markers. The ethanol production operon (PET-operon) containing a cryptic *Z. mo-*

*bilis* promoter, pyruvate decarboxylase, alcohol dehydrogenase and transcriptional terminator was removed as a 5.2 kb EcoRI fragment from pLOI308-10 (Ingram and Conway [1988], supra) and inserted into the EcoRI site of pBR322 to produce pLOI308-11. The plasmid pLOI297 was constructed by inserting the 2.6 kb EcoRI fragment from pCOS2EMBL (Poustka, A., H. R. Rackwitz, A.-M. Firschauf, and H. Lehrach [1984] Proc. Natl. Acad. Sci. USA 81:4129–4133) containing the tetracycline resistance gene in to the SalI site of pLOI295 (Ingram et al. [1987], supra). Cohesive ends were removed by treatment with the Klenow fragment of *E. coli* DNA polymerase (Maniatis et al., supra), prior to the ligation.

Plasmids were introduced into the different strains of *E. coli* by transformation using the calcium chloride procedure of Mandel and Higa (Mandel, M., and A. Higa [1970] J. Mol. Biol. 53:159–162). Selections were made on solid medium containing 2% glucose and tetracycline. Plasmid stability is expressed as the percentage of cells retaining antibiotic markers after 25 generations of growth in the absence of antibiotic selection.

Recombinant strains harboring plasmids with the genes for ethanol production grew as unusually large colonies which became yellow after 24 to 48 hours on solid medium containing a fermentable sugar. In liquid medium, the final cell densities of these recombinants were twice to three times higher than that of the control lacking plasmid. No transformants were obtained after several attempts from ATCC 14948 with pLOI297 or from ATCC 11775 with pLOI308-11. Strain ATCC 11775 did not utilize xylose and recombinants of this strain did not grow to higher densities than the control with xylose as the fermentable sugar, although increased growth was observed with lactose and glucose.

Plasmid stability was examined after growth in medium containing glucose for 25 generations (Table 6). Both plasmids contained the same replicons and were maintained well in all strains except ATCC 8677 and ATCC 8739.

TABLE 6

Stability of pLOI297 and pLOI308-11 after 25 generations of growth with glucose in the absence of antibiotic selection.

| ATCC Strain | Cells retaining plasmid (%) | |
|---|---|---|
| | pLOI297 | pLOI308-11 |
| 8677 | 75 | 85 |
| 8739 | 44 | 47 |
| 9637 | 100 | 90 |
| 11303 | 98 | 98 |
| 11775 | 100 | — |
| 14948 | — | 97 |
| 15224 | 99 | 100 |
| 23227 | 91 | 100 |

Dashed lines indicate no data available.

EXAMPLE 12

Expression of Pyruvate Decarboxylase Activity in Genetically Altered Strains

Pyruvate decarboxylase activity was measured as previously described (Conway et al. [1987], supra; Neale et al. [1987], supra) except that cells were harvested at an O.D. of 4.0, approximately half maximal growth.

The expression of *Z. mobilis* pyruvate decarboxylase activity was examined after growth in the presence of tetracycline (Table 7). With pLOI297, *Z. mobilis* genes are expressed under the control of the *E. coli lac* promoter; pLOI308-11 utilizes a cryptic *Z. mobilis* promoter for expression of PET-operon. Strains ATCC 11303 (pLOI297), ATCC 11775 (pLOI297) and ATCC 15224 (pLOI297) contained the highest levels of activity.

TABLE 7

Expression of *Z. mobilis* pyruvate decarboxylase in *E. coli* strains harboring pLOI297 and pLOI308-11 during growth with glucose.

| ATCC Strain | Pyruvate decarboxylase activity[a] | |
|---|---|---|
| | pLOI297 | pLOI308-11 |
| 8677 | 5.7 | 6.0 |
| 8739 | 0.8 | 1.4 |
| 9637 | 1.1 | 1.4 |
| 11303 | 16.7 | 2.1 |
| 11775 | 17.1 | —[b] |
| 14948 | —[b] | 2.5 |
| 15224 | 16.3 | 1.8 |
| 23227 | 2.3 | 1.7 |

[a]Activity in I.U./mg cell protein.
[b]Dashed lines indicate no data available.

EXAMPLE 13

Ethanol Production of Genetically Altered Strains

Luria broth was modified for fermentation experiments by the inclusion of potassium phosphate buffer (pH 7.0) at a final concentration of 0.2M. Phosphate buffer, complex medium components, and sugars were autoclaved separately and mixed after cooling. Tetracycline was included at a concentration of 10 mg/liter. Inocula were grown from freshly isolated colonies for 24 hours, washed in the fermentation medium to be tested, and added to an initial O.D. 550 nm of approximately 1.0. Fermentations were carried out at 30° C. or 37° C. in 100 ml volumetric flasks containing 80 ml of broth, fitted with rubber septa and 25 gauge needles to allow gas escape. Fermentation flasks were immersed in a temperature-controlled water bath and stirred by a magnetic stirrer at 100 rpm.

Ethanol concentration was measured by gas chromatography as previously described (Dombek, K. M. and L. O. Ingram [1985] Appl. Environ. Microbiol. 51:197–200) and is expressed as percentage by volume. The conversion efficiency was calculated based upon sugar added, assuming that 100% efficiency results in the production of 12.75 ml of ethanol (10.2 g) per 20 g of glucose or xylose and 13.5 ml of ethanol (10.8 g) per 20 g of lactose.

All genetically engineered strains of *E. coli* produced significant amounts of ethanol from sugars (Table 8). Preliminary experiments with strain ATCC 15244 (pLOI297) indicated that higher levels of ethanol were produced in medium containing 0.2M potassium phosphate buffer (pH 7.0). It is anticipated that similar or superior results would be obtained using an automated pH adjustment in place of this buffer. With 15% glucose, higher ethanol levels were produced at 30° C. than at 37° C. after 48 hours. The fermentation of lactose and xylose were examined only at the lower temperature, 30° C. In general, higher levels of ethanol were produced by strains harboring pLOI297 than with pLOI308-11. Strains ATCC 11303 (pLOI297), ATCC 11775 (pLOI297) and ATCC 15224 (pLOI297) produced the highest levels of ethanol after 48 hours from 15% glucose, 5.8% to 6.9% by volume. Most strains were less tolerant of xylose in initial experiments and comparisons of fermentation were carried out using 8% xylose. Strains ATCC 9637 (pLOI297), ATCC 11303

(pLOI297), and ATCC 15224 (pLOI297) produced the highest levels of ethanol (4.8% to 5.2%) from 8% xylose after 72 hours. All strains grew well in 15% lactose. Strains ATCC 11303 (pLOI297) and ATCC 15224 (pLOI297) produced the highest levels of ethanol from lactose after 48 hours, 6.1% and 5.6%, respectively.

TABLE 8

Ethanol produced in batch fermentation from glucose (48 hours), xylose (72 hours), and lactose (48 hours) by *E. coli* strains harboring pLOI297 and pLOI308-11.

| | | Ethanol (%, v/v) produced by *E. coli* strains (ATCC numbers) | | | | | | | |
|---|---|---|---|---|---|---|---|---|---|
| Carbohydrate | Plasmid | 8677 | 8739 | 9637 | 11303 | 11775 | 14948 | 15224 | 23227 |
| 15% glucose | pLOI297[a] | 2.4 | 4.7 | 4.2 | 4.3 | 4.8 | — | 4.8 | 0.9 |
| 15% glucose | pLOI308-11[a] | 3.6 | 1.4 | 2.1 | 1.3 | — | 3.4 | 2.8 | 1.3 |
| 15% glucose | pLOI297[b] | 3.2 | 4.7 | 4.1 | 5.8 | 6.9 | — | 6.1 | 3.1 |
| 15% glucose | pLOI308-11[b] | 5.8 | 5.0 | 3.5 | 1.5 | — | 3.8 | 3.0 | 3.2 |
| 15% lactose | pLOI297[b] | 2.3 | 4.4 | 5.3 | 6.1 | 4.5 | — | 5.6 | 3.7 |
| 15% lactose | pLOI308-11[b] | 2.3 | 2.1 | 3.4 | 0.9 | — | 2.9 | 2.7 | 3.0 |
| 8% xylose | pLOI297[b] | 0.9 | 4.1 | 4.8 | 5.2 | — | — | 4.8 | 1.2 |
| 8% xylose | pLOI308-11[b] | 2.0 | 2.8 | 2.8 | 1.2 | — | 2.0 | 3.5 | 1.0 |

Dashed lines indicate no data available.
[a]Incubated at 37° C.
[b]Incubated at 30° C.

Based upon these comparative studies, strains ATCC 11303 (pLOI297) and ATCC 15224 (pLOI297) appeared to be the best constructs for ethanol production. The time course of growth and ethanol production were examined with both strains in 12% glucose, 12% lactose, and 8% xylose (FIG. 1). Cell mass increased approximately 10-fold, reaching a final density of 3.6 g dry weight/liter. With xylose, cell mass increased at half the rate observed with glucose or lactose. Ethanol production and growth were approximately linear for the three sugars until the concentration of ethanol reached 5%.

To compute the conversion efficiency of sugar to ethanol, final ethanol concentrations after 120 hours were averaged from three sets of experiments (Table 6). The final concentration of ethanol in cultures grown with 12% glucose was 7.2% (by vol.), representing 94% of theoretical yield from glucose. With 12% lactose, the final ethanol concentration was 6.5%, 80% of the theoretical yield from lactose. With 8% xylose, we consistently obtained yields of 100% and higher. These high yields during slower growth with xylose may reflect the conversion of pyruvate from the catabolism of complex nutrients into ethanol, in addition to pyruvate from glucose.

The rate of ethanol production was computed from the graphs in FIG. 1 and are summarized in Table 9. Volumetric productivity of ethanol ranged from 1.4 g/liter per hour for glucose to 0.64 g/liter per hour for xylose. Specific productivity of ethanol was highest during the initial growth period for each of the three sugars. The highest productivity was obtained with glucose, 2.1 g ethanol/g cell dry weight per hour. The highest yield of ethanol per g of sugar was obtained with xylose, exceeding the maximal theoretical yield for sugar alone.

TABLE 9

Averaged kinetic parameters for ethanol production by ATCC 11303(pLOI297) and ATCC 15224(pLOI297).

| Sugar | Volumentric[a] Productivity | Specific[b] Productivity | Yield[c] | Efficiency[d] | Ethanol[e] |
|---|---|---|---|---|---|
| 12% glucose | 1.4 | 2.1 | 0.48 | 95% | 58 |
| 12% lactose | 1.3 | 2.0 | 0.43 | 80% | 52 |
| 8% xylose | 0.6 | 1.3 | 0.52 | 102% | 42 |

[a]g ethanol/liter per hour
[b]g ethanol/g cell dry weight per hour
[c]g ethanol/g sugar
[d]ethanol produced/theoretical maximum from sugar substrate × 100
[e]final ethanol concentration in g/liter Experiments were conducted with ATCC 11303 (pLOI297) to examine ethanol production from arabinose, galactose, and mannose. Ethanol concentrations of 3% to 4% were obtained after 48 hours at 30° C. but were not investigated further. These sugars were metabolized by pathways similar to those for glucose and xylose and would be expected to produce analogous yields (Lin, E.C.C. [1987] "Dissimilatory pathways for sugars, polyols, and carboxylates," In F. C. Neidhardt, J. L. Ingraham, K. B. Low, B. Magasanik, and M. Schaechter [eds], *Escherichia coli* and *Salmonella typhimurium*, Vol. 1, pp. 244–284. American Society for Microbiology, Washington, D.C.).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An *Escherichia coli*, which has been transformed with *Zymomonas mobilis* genes coding for alcohol dehydrogenase and pyruvate decarboxylase wherein said genes are expressed at sufficient levels to confer upon said *Escherichia coli* transformant the ability to produce ethanol as a fermentation product.

2. The *Escherichia coli*, according to claim 1, wherein the *Escherichia coli*, prior to transformation, is selected from the group consisting of ATCC 8677, ATCC 8739, ATCC 9637, ATCC 11303, ATCC 11775, ATCC 14948, ATCC 15224, and ATCC 23227.

3. The *Escherichia coli*, according to claim 1, wherein said *Escherichia coli* has been transformed with a plasmid selected from the group consisting of pLOI308-10, pLOI297, and pLOI308-11.

4. The *Escherichia coli*, according to claim 3, wherein said *Escherichia coli* has been transformed with pLOI297.

5. A method for the production of ethanol, said method comprising transforming an *Escherichia coli* with *Zymomonas mobilis* genes coding for pyruvate decarboxylase and alcohol dehydrogenase wherein said genes are expressed by the transformed *Escherichia coli* at sufficient levels to result in the production of ethanol as a fermentation product when said *Escherichia coli* is grown in an appropriate medium.

6. The method, according to claim 5, wherein said *Escherichia coli* is transformed with a plasmid selected from the group consisting of pLOI308-10, pLOI297, and pLOI308-11.

7. The method, according to claim 6, wherein said *Escherichia coli* has been transformed with pLOI297.

* * * * *